United States Patent [19]
Gresch

[11] Patent Number: 4,794,013
[45] Date of Patent: Dec. 27, 1988

[54] PROCESS FOR EXTRACTING OF LIQUID FROM A RESIDUAL SUBSTANCE

[75] Inventor: Walter Gresch, Niederweningen, Switzerland

[73] Assignee: Bucher-Guyer AG, Niederweningen, Switzerland

[21] Appl. No.: 71,373

[22] Filed: Jul. 9, 1987

Related U.S. Application Data

[63] Continuation-in-part of Ser. No. 748,960, Jun. 26, 1985, abandoned.

[51] Int. Cl.⁴ .............................................. A23L 2/04
[52] U.S. Cl. ..................................... 426/489; 426/51; 426/495
[58] Field of Search ............ 426/489, 495, 387, 330.5, 426/599, 51

[56] References Cited

U.S. PATENT DOCUMENTS

| | | | |
|---|---|---|---|
| 2,559,459 | 7/1951 | Peebles et al. | 426/489 |
| 4,083,779 | 4/1978 | Combe et al. | 426/495 |
| 4,483,875 | 11/1984 | Dorreich | 426/51 |
| 4,551,341 | 11/1985 | Blanie et al. | 426/489 |

Primary Examiner—George Yeung
Attorney, Agent, or Firm—Edmund M. Jaskiewicz

[57] ABSTRACT

A process and apparatus for extracting a liquid from a filtered residual substance, such as retentate resulting from an ultrafiltration during fining or clarification of raw juice from agricultural products. The residues are mixed with the expressed pomace in a separate processing and the mixture is subjected to a further juice extraction.

8 Claims, 3 Drawing Sheets

PROCESS FOR EXTRACTING OF LIQUID FROM A RESIDUAL SUBSTANCE

RELATED APPLICATION

This application is a continuation-in-part of Ser. No. 748,960 filed June 26, 1985 and now abandoned.

The present invention relates to the extraction of liquid from residues of dregs, macromolecules and colloidally dissolved particles separated from a filtered residual substance, more particularly, to a process and apparatus for the extraction of liquid from residues resulting from the extraction of juices from agricultural products such as fruit, grain, berries, vegetables and the like.

It has been known to subject dregs, macromolecules and colloidally dissolved parts separated from a filtered residual substance to a further extraction in order to optimize the extraction of liquid from agricultural products and to increase the yield. In connection with such a process it has also been known to subject the raw juices to a so-called ultrafiltration for fining or clarification of these juices. The use of chemicals and/or natural fining agents has the disadvantage that the costs of the process are increased.

It has been proposed to feed or return the retentate resulting from the ultrafiltration process to the pressed out mash in order to extract an additional amount of juice from this residual product. This proposal is based on the premise that the mash in the press acts as a filter on the retentate and retains from the retentate the materials which are undesired in the final juice product. However, this process has the disadvantage that certain materials in the retentate can have a negative and adverse effect on the quality of the juice extracted from the fresh mash. In addition, with batch pressing such a process is uneconomical in the situation of larger amounts of retentate to achieve an adequate filtering action. It is also necessary in such a process that for a semi-batch ultrafiltration, the resulting excess retentate must be stored temporarily and as a result later utilization of this retentate leads to a poorer retentate juice quality. Further, the filtering action of the mash is considerably impaired by the presence of the fine solid components in the retentate.

It is therefore the principal object of the present invention to provide a novel and improved process and apparatus for the extraction of liquid from residues resulting from the extraction of juices from agricultural products.

It is another object of the present invention to provide such a process and apparatus which enables an at least partially continuous operation and which eliminates the necessity for using chemical and/or natural fining agents.

It is a further object of the present invention to provide such a process and apparatus which significantly minimizes any adverse effects on the retentate upon the quality of the juice product.

It is an additional object of the present invention to provide such a process and apparatus which optimizes the yield and quality of the final juice product and which avoids any impairment of the filtering action of the mash.

The objects of the present invention are achieved and the disadvantages of the prior art as discussed above are eliminated by mixing the residue resulting during fining or clarification of juices with the at least partially pressed out pomace for a separate processing operation. In this procedure, the extraction of juice from the fresh mash remains undisturbed and a selective separation of the qualities of juices can be performed even when sizable quantities of mash are to be processed. In addition, an amount of pomace resulting from several pressing out operations can be processed with the retenate which results in a more economical operation.

In one form of the present process, the pomace processed with the retentate, is subjected to another juice extraction. For this purpose, it is advantageous if the pomace is subjected to an enzyme treatment to break down the cell walls. Preferably, the retentate can be used as an enzyme carrier. Use of the retentate as the enzyme carrier provides the possibility that in the case of subsequent concentration of the juice, little or no diluting water must be evaporated. In addition, the heat given off by the ultrafiltration installation to the retentate promotes the enzymatic reaction capacity of the pomace mixture.

The additional installation costs necessitated by the separate pomace juice extraction are significantly offset by the fact that the press is now reserved completely for juice extraction from fresh mash which avoids a loss of juice quality and press performance. In an alternative process step, the juice extracted from the pomace mixture may be returned back into the process at the ultrafiltration installation. The various volatile flavors and aromas can then escape in an evaporator installation or an off-flavor stripper so that the resulting concentrate in comparison with the raw juice concentrate does not exhibit any change in taste. In this connection, it is advantageous if the extracted juice is returned to the process after flavor recovery.

According to one aspect of the present invention, a process for the extraction of liquid from residues of dregs, macromolecules and colloidally dissolved particles separated from a filtered residual substance, particularly from residues resulting from the extraction of juices from agricultural products may comprise the steps of subjecting an agricultural product to an extraction to obtain a raw juice and an at least partially pressed out pomace. The juice is subjected to a fining or clarification to form a retentate which is then mixed with the at least partially pressed out pomace in a separate processing step.

An apparatus for carrying out such a process may comprise a press having means for pressing out an agricultural product mash to extract a raw juice therefrom and to obtain an at least partially pressed out pomace. Means are then provided either within the press or externally of the press for mixing a process liquid obtained from a fining or clarification of the raw juice with the at least partially pressed out pomace.

Other objects and advantages of the present invention will be readily apparent upon reference to the accompanying description when taken in conjunction with the following drawings, which are exemplary, wherein.

Proceeding next to the drawings, wherein like reference symbols indicate the same parts throughout the various views, a specific embodiment and modifications of the present invention will be described in detail.

Figure 1:
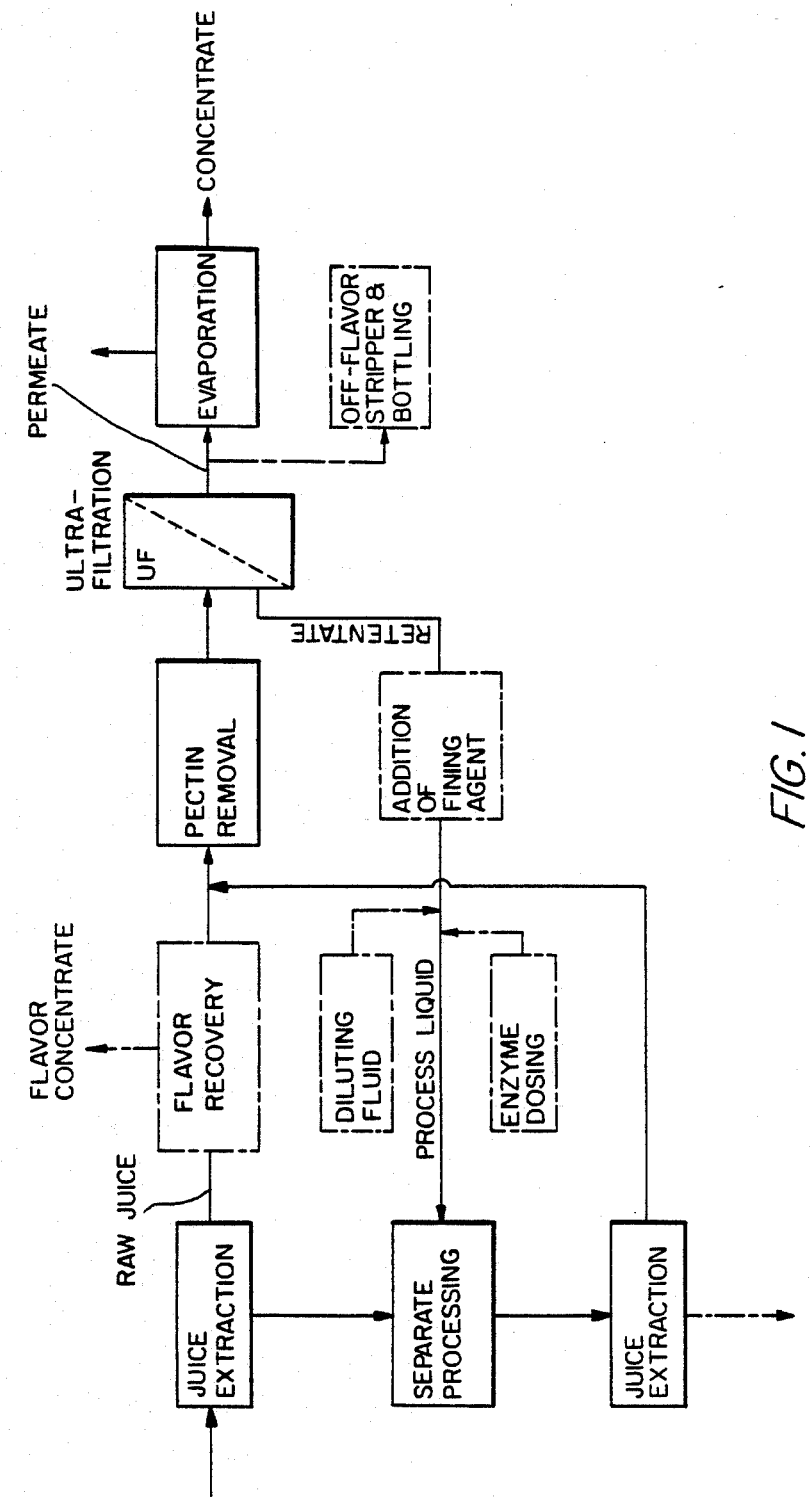
FIG. 1 is a diagramatic representation of the process and apparatus according to the present invention.

The top row of blocks in FIG. 1 represents diagramatically a typical connection of individual pieces of apparatus in an installation for extracting juice from fruit, grain, berries, vegetables and the like. This installation is provided with an ultrafiltration device for the fining of the juice in the mainstream. Ultrafiltration is a technique for separating dissolved molecules on the basis of size, by passing a solution through an extremely fine membrane filter.

Juice extraction at the beginning of the installation is carried out by a press to which the product is fed in the form of mash. Pressing of the mash is generally carried out in several cycles or squeezings. The pressed out pomace is removed from the press for separate processing according to the present invention. The resulting raw juice is fed from the press to a flavor recovery device.

The raw juice is then supplied to a pectin removal device in which any pectins contained in the juice are decomposed. Subsequently, the juice is then supplied to an ultrafiltration device in which the juice is subjected to fining. The ultrafiltration operation normally occurs at 50°-55° C. and separates the raw juice into a clear juice or permeate and a resulting residue consisting of dregs, colloidally dissolved particles, macromolecules, such as proteins, starch and the like, this residue is called the retentate. The clear juice, or permeate, is then passed through an evaporation apparatus for concentrating or through an off-flavor stripper for bottling.

According to the present invention, the retentate to which may be added enzymes, particularly cellullase enzymes, and/or diluting liquid is mixed with the pomace resulting from the juice extraction press and then reprocessed in a separate processing operation.

For binding and subsequent separation of macromolecules and colloidally dissolved particles during processing of the pomace with the retentate, it is preferable that a fining agent, for example, silica sol, gelatin, bentonite, tannin, is added to the retentate.

Since the ultrafiltration can be performed cold or at room temperatures, the process liquid can be heated by a heat exchanger to the required temperature in order to attain a suitable reaction temperature for enzymizing. Enzymizing occurs during processing. The enzyme is added to the retentate on its path to the processing with the pomace. Juice is then extracted from the process mixture in a press. The extracted liquid is then introduced back into the process line after the flavor recovery device and subjected to a further ultrafiltration.

The resulting juice can also be utilized in another manner. With an ultrafiltration apparatus which is operating in batch or semi-continuously, the enzyme can be mixed with the retentate stored in the temporary container of the ultrafiltration apparatus, preferably before the periodic cleaning of the ultrafiltration apparatus. Also, the other remaining adjuvants or supplements used in the process can be introduced at this time.

The installation, in order to carry out the process of the present invention is provided with several separate processing or extracting devices. A press is preferably employed because of a further extraction of juice from the processed pomace. Those presses are preferable in which the pomace can be sprayed or sprinkled as uniformly as possible with the process liquid.

The present process permits a small quantity ratio of process liquid and pomace. Therefore, in spite of a high yield with a small amount of retentate formed it is necessary to use only little or no diluting fluid for an enzymatic pomace juice re-extraction. If the quantity ratio should be reversed, i.e., if the retentate amount is relatively high, then binders, for example, saw dust, silica sol, can still be added during later processing of the pomace. This measure promotes the filtration of the dregs from the retentate. The greatest possible uniformity of mixing of the process liquid and pomace promotes the enzyme reaction and improves the filtration of the retentate.

Figure 2:
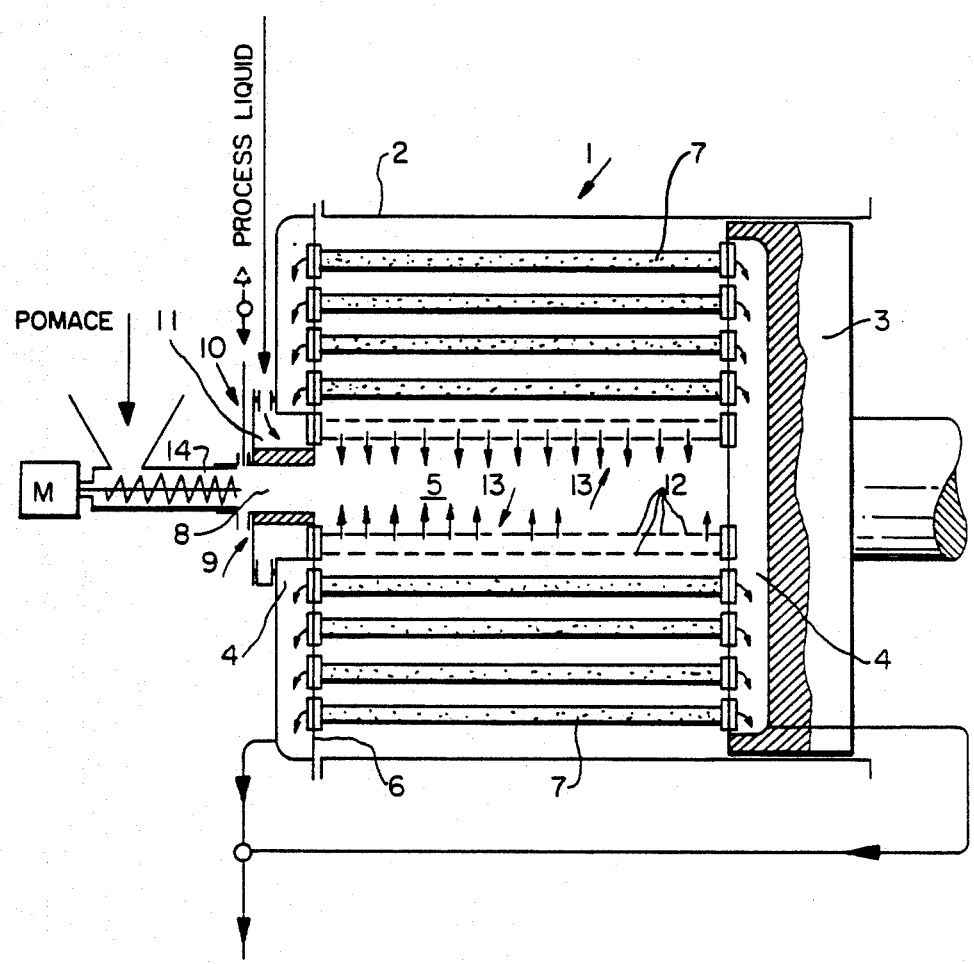
FIG. 2 is a longitudinal sectional view through a juice extraction device according to the present invention.

In FIG. 2 there is illustrated an apparatus for carrying out the process of the present invention in which the processing of the pomace is performed by a press 1. The press 1 is enclosed within a rotating housing 2 at one end of which there is a powered movable piston 3 so as to move axially within the housing and at the other end of the container is a juice receptable 4. In the present embodiment, the piston 3 is also provided with a juice receptacle compartment 4 on its side directed toward a mash space 5 within the housing 2. The end of the housing provided with the juice receptacle 4 is also provided with a separation or counter-pressure wall 6 which separates the juice receptacle 4 from the mash space 5. A plurality of flexible drainage filter element 7 have their ends connected between the wall 6 and piston 3. The juice which is pressed from the mash by the movement of the piston within the housing 2 flows along the drainage filter elements 7 into juice receptacle 4 and from there to subsequent steps of the process. The general principle of such a press is known in the art.

The press 1 is provided with a feed opening 8 positioned concentrically with the axis of rotation of the container 2. According to the present invention, an additional structure is utilized with the press 1. Next to the feed opening 8 which is constructed as a rotating inlet 9 for the mash, there is another central liquid inlet 10 through which process liquid is supplied into the press. This inlet 10 is indicated diagramatically and discharges the process liquid into an intake 11 connected to the rotating housing 2 for this purpose. The process liquid then passes from the intake 11 into the distribution hoses or tubes 13 which are stretched between counterpressure wall 6 and piston 3 and the distribution hoses are provided with perforations 12. The pomace is supplied through a pipe 14 into the container 2 for mixing with the process liquid and the rotation of the container promotes this mixing process.

In a known manner, the press is emptied after extraction of juice from the process pomace by axially shifting the housing 2 in an axial direction.

According to the present invention, the pomace and process liquid could also be supplied to the mash or press space 5 through a cover in the housing which is periodically opened.

Figure 3:
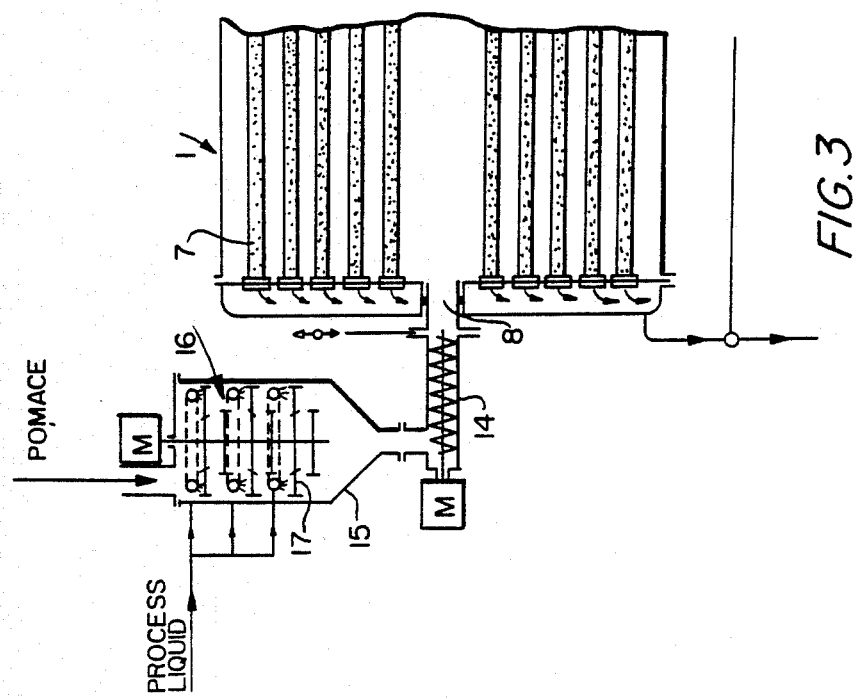
FIG. 3 is a longitudinal sectional view through a portion of a juice extraction device and a mixing device connected upstream thereof.

In FIG. 3, there is illustrated a processing structure for the pomace disposed externally of the press 1 which is provided with a central feed opening 8 which has been found to be advantageous for charging of the press. This apparatus is intended only for the separate processing and juice extraction of the pomace after it has been thoroughly mixed with the process liquid. Extraction of juice from the fresh mash is preferably carried out with other presses which operate separately from this process of the press illustrated in FIG. 3. When an external processing is employed as in FIG. 3, the central liquid inlet of FIG. 2 can be omitted from the press 1 used in the structure of FIG. 3.

As a further modification, the mash supply pipe 14 can be connected to a continuous flow spray mixer 15 in which there is a spray mixing device 16 to bring about a thorough mixing of the pomace and process liquid. The spray mixing device 15 is also provided with several mixing members 17 and has a plurality of circular pipes or tubes for uniform distribution of the liquid within the mixer. The axis of rotation of the mixing members may either be vertical or horizontal. In a vertical arrangement, the pomace is treated more gently since a thorough mixing time together with a slower speed of the mixing member 17 is shorter than in the case of a horizontal axis of rotation. A more gentle treatment of the pomace enables a more effective and efficient pressing of the pomace mixture to be attained.

Figure 4:
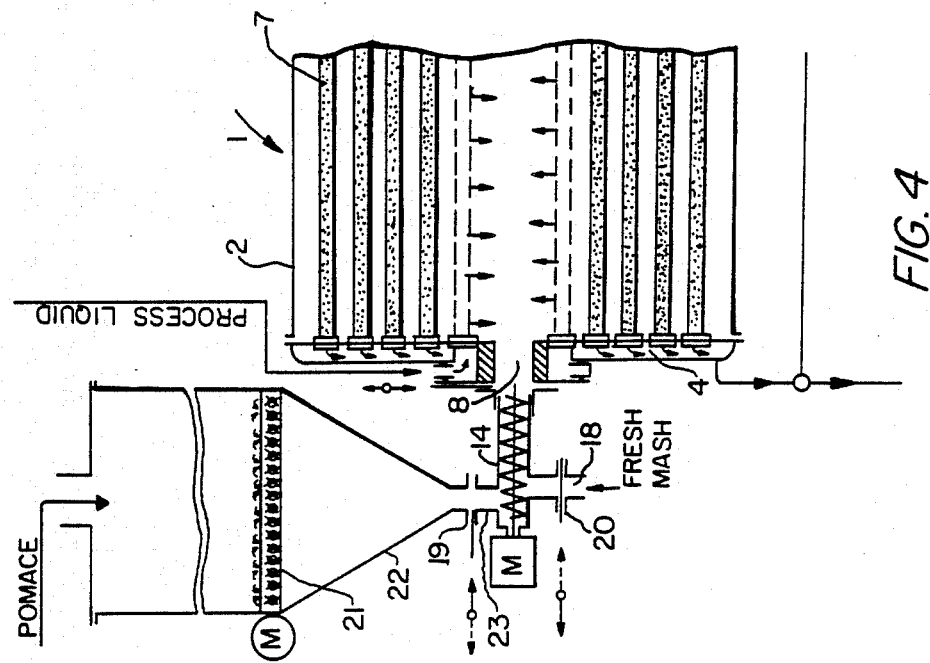
FIG. 4 is a longitudinal sectional view through a portion of a juice extraction device having a pomace storage container connected upstream.

In FIG. 4, there is illustrated a further form of press with an external processing structure with a pomace storage connected upstream. Processing of the pomace with the process liquid occurs within the press housing 2 as described for the structure of FIG. 2.

Unlike the apparatus of FIG. 2 the structure of FIG. 4 makes it possible to also extract juice from fresh mash by a separate operation in addition to the processing and juice extraction from the pomace enriched with the process liquid.

The press housing 2 is charged along its axis of rotation through opening 8 as in FIG. 2. The mash supplied by 14 is connected on the one hand to a pomace storage container 22 and to a pipe 18 for supplying fresh mash. The storage container 22 has a discharge pipe 23 and both connecting pipes 18 and 23 can be selectively controlled by cut-off valves 20 and 19 respectively. A driven discharge or dispensing device 21 is mounted in the pomace storage container 22 to enable the amount of pomace to be fed for processing to be precisely determined.

Thus it is apparent that the present invention has disclosed a simplified yet effective structure and process for significantly improving the yield and quality of juices extracted from agricultural products.

Juice is extracted from agricultural products such as vegetables and fruits so as to obtain a final juice product of a selected quality. The extracted juice is subjected to a fining or clarification step and the residue resulting from this fining is mixed with at least a partially pressed out pomace remaining from the first extraction step. This residue is mixed with the pomace separately from the first extraction step so that the extraction of juice from the fresh mash remains undisturbed. The pomace mixed with the residue is then subjected to a subsequent second extraction and the additional juice resulting from this second extraction is also returned back into the process at the fining step. The result is to improve the yield and quality of juices extracted from agricultural products without any possibility of the residue having any negative and adverse effect on the quality of the juice extracted from the fresh mash. In the prior art, particularly the U.S. Pat. No. 2,559,459 to Peebles et al, the residue from the fining step is returned to the pressed out mash in order to extract additional juice from the residue. The present invention, however, avoids any negative and adverse effects on the quality of the juice extracted from the mash by mixing the residue with pomace resulting from the first extraction step. The juice extracted from the pomace mixture is returned back into the process and one place in the process to which the extracted juice may be returned is at the fining step.

In the prior art there is disclosed a process for obtaining a dried solid product from vegetables by the expelling of juice from fresh vegetable material. The expelled juice is then subjected to a separation and solids resulting from this separation step are then dried together with cake obtained from the step of expelling the juice. While the mixture of cake and solids is dried to remove liquids therefrom, there is no contemplation of retaining these liquids and then returning these liquids back to the process. The cake and solids are subjected to a conventional drying step and presumably any liquids resulting from this drying escape into the atmosphere or are discharged in some other manner.

The prior art process is in direct contrast to this invention wherein the end product of this invention is a liquid juice and liquids obtained from the second extraction step are returned back to the process to significantly improve the yield and quality of the final juice product.

The final product in the prior art is a dried solid whereas the final product in the subject process is a liquid juice. The problem of obtaining a liquid juice by subjecting a residue obtained from a fining step to a further second extraction together with pomace obtained from a first extraction step is proposed and solved by applicant and is altogether different from problems proposed and solved by the prior art.

The present process involves an extraction of juices by an expelling or physical treatment of the juices as opposed to any drying process which would affect adversely the chemical composition of the resulting juices. The use of conventional drying processes would drive off certain aromatic portions of the juices which in turn adversely affect the taste and quality of the juice.

Thus it can be seen that applicant's process provides a considerably higher and more efficient use of the original mash which in turn results in achieving a much larger yield of juice. At the same time it is possible to supply the mash or the partially pressed out pomace with the residue obtained during the juice extraction process to further increase the yield of juice.

With the present process large quanities of mash can be processed without adversely affecting the yield and efficiency of the process. If desired, the different mashes or qualities of pomace can be subjected to the different steps of applicant's process in separate operations and apparatus.

It will be understood that this invention is susceptible to modification in order to adapt it to different usages and conditions, and accordingly, it is desired to comprehend such modifications within this invention as may fall within the scope of the appended claims.

What is claimed is:

1. A process for forming a juice product of a selected quality by the extraction of liquid from residues of dregs, macromolecules and colloidally dissolved particles separated from a filtered residual substance, including residues resulting from the extraction of juices from agricultural products comprising fruit, grain, berries and vegetables, the steps of subjecting an agricultural product to a first extraction to obtain a raw juice and an at least partially pressed out pomace, subjecting the juice to a fining or clarification operation to form a clear juice and a retentate consisting of a residue of dregs, macromolecules and colloidally dissolved particles, mixing the retentate with the at least partially pressed out pomace in a further processing step subsequent to and separate from the first extraction step to form a processed pomace so that the first extraction of juice from the agricultural product remains undisturbed, and subjecting the processed pomace to a second juice extraction separate from the first extraction to obtain additional raw juice.

2. A process as claimed in claim 1 wherein said fining or clarification operation comprises untrafiltration.

3. A process as claimed in claim 1 and subjecting the partially pressed out pomace to an enzyme treatment to break down the cell walls.

4. A process as claimed in claim 3 wherein the retentate is used as a carrier of an enzyme.

5. A process as claimed in claim 2 and returning the juice extracted from the processed pomace back into the process at the ultrafiltration step.

6. A process as claimed in claim 1 and subjecting the raw juice to a flavor recovery step, and returning the juice extracted from the processed pomace back to mix with the raw juice from the flavor recovery step.

7. A process as claimed in claim 1 and the step of adding a binder to the processed pomace.

8. A process as claimed in claim 1 and the step of adding a fining agent to the retentate or the processed pomace.

* * * * *